United States Patent
Bailey et al.

(10) Patent No.: US 7,397,895 B2
(45) Date of Patent: *Jul. 8, 2008

(54) MOBILE COMPUTERIZED TOMOGRAPHY (CT) IMAGING SYSTEM WITH CORDLESS AND WIRELESS CAPABILITIES

(75) Inventors: Eric M. Bailey, Hampton, NH (US); Andrew P. Tybinkowski, Boxford, MA (US); Bernard Gordon, Manchester, MA (US); Gerard Riley, Chester, NH (US); Michael T. Limoli, Merrimac, MA (US); Daniel A. Garland, Salisbury, MA (US)

(73) Assignee: NeuroLogica Corp., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/653,493

(22) Filed: Jan. 16, 2007

(65) Prior Publication Data

US 2007/0183588 A1    Aug. 9, 2007

Related U.S. Application Data (63) Continuation-in-part of application No. 11/193,941, filed on Jul. 29, 2005, now Pat. No. 7,175,347.

(60) Provisional application No. 60/670,164, filed on Apr. 11, 2005, provisional application No. 60/593,001, filed on Jul. 30, 2004.

(51) Int. Cl.
*H05G 1/10* (2006.01)
*H05G 1/02* (2006.01)

(52) U.S. Cl. .................. 378/102; 378/198

(58) Field of Classification Search ............ 378/4, 378/19, 101, 102, 193–198
See application file for complete search history.

(56) References Cited

U.S. PATENT DOCUMENTS

| | | | |
|---|---|---|---|
| 3,603,975 A | | 9/1971 | Gordon |
| 5,425,069 A | * | 6/1995 | Pellegrino et al. ............ 378/198 |
| 5,499,284 A | * | 3/1996 | Pellegrino et al. ............ 378/198 |
| 5,887,047 A | | 3/1999 | Bailey et al. |
| 5,982,843 A | | 11/1999 | Bailey et al. |
| 6,108,396 A | | 8/2000 | Bechwati et al. |
| 6,199,233 B1 | * | 3/2001 | Kantrowitz et al. ............ 5/601 |
| 6,256,404 B1 | | 7/2001 | Gordon et al. |
| 6,285,028 B1 | | 9/2001 | Yamakawa |
| 6,374,937 B1 | * | 4/2002 | Galando et al. ............ 180/211 |
| 6,396,902 B2 | | 5/2002 | Tybinkowski et al. |
| 6,813,374 B1 | | 11/2004 | Karimi et al. |

(Continued)

*Primary Examiner*—Irakli Kiknadze
(74) *Attorney, Agent, or Firm*—Pandiscio & Pandiscio (57) ABSTRACT

A mobile CT imaging system comprising a frame; a CT imaging unit mounted to the frame, wherein the CT imaging unit is adapted to scan anatomical objects and generate images of the same; a transport mechanism mounted to the frame, wherein the transport mechanism comprises a fine movement mechanism for moving the CT imaging unit precisely, relative to the patient, during scanning; an onboard networking unit mounted to the frame, wherein the on-board networking unit is adapted to connect the CT imaging unit to a workstation, hospital PACs system or other IT network without requiring the use of conventional physical cabling during the same; and an on-board power unit mounted to the frame, wherein the onboard power unit is adapted to provide the electrical power needed to operate the CT imaging unit, transport mechanism and networking unit without requiring the use of conventional physical cabling during the same.

15 Claims, 5 Drawing Sheets

U.S. PATENT DOCUMENTS 6,857,778 B2    2/2005  Mun et al.
7,016,467 B2 *  3/2006  Brooks ................. 378/102

2004/0146142 A1 *  7/2004  Maijala ................. 378/102

* cited by examiner

MOBILE COMPUTERIZED TOMOGRAPHY (CT) IMAGING SYSTEM WITH CORDLESS AND WIRELESS CAPABILITIES

REFERENCE TO PENDING PRIOR PATENT APPLICATION

This patent application is a continuation-in-part of prior U.S. patent application Ser. No. 11/193,941, filed Jul. 29, 2005 now U.S. Pat. No. 7,175,347 by Andrew P. Tybinkowski et al. for ANATOMICAL IMAGING SYSTEM WITH CENTIPEDE DRIVE, which patent application in turn claims benefit of:

(i) prior U.S. Provisional Patent Application Ser. No. 60/670,164, filed Apr. 11, 2005 by Andrew P. Tybinkowski et al. for. ANATOMICAL IMAGING SYSTEM WITH CENTIPEDE DRIVE; and (ii) prior U.S. Provisional Patent Application Ser. No. 60/593,001, filed Jul. 30, 2004 by Bernard Gordon et al. for ANATOMICAL SCANNING SYSTEM.

The three above-identified patent applications are hereby incorporated herein by reference.

FIELD OF THE INVENTION

This invention relates to anatomical imaging systems in general, and more particularly to Computerized Tomography (CT) imaging systems.

BACKGROUND OF THE INVENTION

Strokes are currently the third leading cause of death in the United States, causing approximately 177,000 deaths per year, and strokes are currently the number one cause of long-term disability in the United States, currently affecting nearly 5 million people. Strokes are caused by an abrupt interruption of the blood supply to the brain or spinal cord, thereby depriving the tissue of oxygen and resulting in tissue damage.

Strokes typically occur in one of two forms: (i) hemorrhagic stokes, which occur with the rupture of a blood vessel; and (ii) ischemic strokes, which occur with the obstruction of a blood vessel.

Rapid diagnosis is a key component of stroke treatment. This is because the treatment for an ischemic stroke may be contra-indicated for the treatment for a hemorrhagic stroke and, furthermore, the effectiveness of a particular treatment may be time-sensitive. More particularly, the current preferred treatment for an acute ischemic stroke, i.e., the administration of tPA to eliminate blood clots, is contra-indicated for a hemorrhagic stroke. Furthermore, the clinical data suggests that the medication used to treat ischemic strokes (i.e., tPA) is most effective if it is administered within 3 hours of the onset of the stroke. However, current diagnosis times, i.e., the time needed to identify that the patient is suffering from a stroke and to identify the hemorrhagic or ischemic nature of the stroke, frequently exceeds this 3 hours window. As a result, only a fraction of current ischemic stroke victims are timely treated with tPA.

Imaging is generally necessary to properly diagnose (and hence properly treat) a stroke. More particularly, imaging is generally necessary to: (i) distinguish strokes from other medical conditions; (ii) distinguish between the different types of strokes (i.e., hemorrhagic or ischemic); and (iii) determine appropriate treatments (e.g., the administration of tPA in the case of an ischemic stroke).

Computerized Tomography (CT) has emerged as the key imaging modality in the diagnosis of strokes. CT scanners generally operate by directing X-rays into the body from a variety of positions, detecting the X-rays passing through the body, and then processing the detected X-rays so as to build a computer model of the patient's anatomy. This computer model can then be visualized so as to provide images of the patient's anatomy. It has been found that such CT scanning, including non-enhanced CT scanning, CT angiography scanning and CT perfusion scanning, is able to provide substantially all of the information needed to effectively diagnose (and hence properly treat) a stroke.

Unfortunately, in practice, the CT machine is typically located in the hospital's radiology department and the patient is typically received in the hospital's emergency room, and the "round-trip" time between the emergency room and the radiology department can frequently involve substantial delays, even in the best of hospitals. As a result, the time spent in transporting the patient from the emergency room to the radiology department and then back again can consume critical time which can compromise proper treatment of the patient (e.g., it can prevent ischemic stroke victims from being timely treated with tPA).

Thus, there is an urgent need for a new and improved CT machine which is particularly well suited for use in stroke applications. More particularly, there is an urgent need for a small, mobile CT machine which can be pre-positioned in the emergency room and moved to the patient so that the patient can be scanned at their current location, thus effectively eliminating "round-trip" delays and dramatically reducing the time needed to properly diagnose the patient. It is also important that the CT machine be relatively inexpensive, so as to facilitate its rapid proliferation and widespread use, e.g., pre-positioning in substantially all hospital emergency rooms and wide availability in outlying, low-volume settings (e.g., rural hospitals, ships, etc.).

In this respect it should also be appreciated that current CT scanners are typically accompanied by a significant amount of physical cabling. This physical cabling generally takes the form of (i) electrical cables used to deliver electrical power to the CT scanner, and (ii) networking cables used to connect the CT scanner to a workstation, whereby to permit medical personnel to issue scanning instructions to the CT scanner using the workstation, and whereby to enable the CT scanner to send images and scanner data to the workstation for viewing by medical personnel. The workstation can, in turn, be connected to a hospital PACs (Picture Archive and Communication) system or other IT network, so as to permit the CT scanner to be controlled from remote locations and so as to permit images and scanner data to be viewed by medical personnel at remote locations. Alternatively, the CT scanner can be directly connected to a hospital PACs system or other IT network.

The aforementioned physical cabling generally does not present significant issues with conventional CT scanners, since such conventional CT scanners are designed for fixed-position installations. Thus, with fixed-position CT scanners, the disposition of the physical cabling can be addressed at the time of CT scanner installation so as to make the physical cabling relatively inobtrusive (e.g., the physical cabling can be carefully positioned so that it is out of the way of patients and medical personnel).

However, if the CT scanner is to be highly mobile so that the CT scanner can be brought to the bedside of the patient, conventional physical cabling presents a significant problem, since it can interfere with the delivery of time-critical medical treatment and present a physical hazard to medical personnel focused on delivering such medical treatment.

By way of example but not limitation, suppose a patient arrives in an emergency room presenting symptoms of stroke. In this situation, it is imperative that CT scanning be effected as quickly as possible, even as other medical testing and/or treatment is being administered to the patient. Medical personnel must work quickly and efficiently in this situation, with their focus on the delivery of time-critical patient care. If a mobile CT scanner were equipped with conventional physical cabling, bringing the mobile CT scanner to the patient would require the introduction of this conventional physical cabling to the point of care. This physical cabling would present a significant intrusion into the point of care, complicating the delivery of time-critical medical treatment and presenting a physical hazard to medical personnel working around the patient. This is particularly true where the mobile CT scanner is deployed hurriedly, e.g, in the case of a possible stroke patient just arriving at an emergency room.

Thus, there is a need for a new and improved approach for (i) providing the electrical power needed to operate the mobile CT scanner, and (ii) connecting the CT scanner to a workstation, hospital PACs system or other IT network, all without the use of the physical cabling normally associated with a conventional CT scanner.

SUMMARY OF THE INVENTION

In accordance with the present invention, there is provided a novel approach for (i) providing the electrical power needed to operate the mobile CT scanner, and (ii) connecting the CT scanner to a workstation, hospital PACs system or other IT network, all without the use of the physical cabling normally associated with a conventional CT scanner.

And there is provided a novel mobile CT machine with cordless and wireless capabilities, such that the novel CT machine does not require physical cabling to (i) provide the electrical power needed to operate the mobile CT scanner, and (ii) connecting the CT scanner to a workstation, hospital PACs system or other IT network.

In one form of the invention, there is provided a mobile CT imaging system comprising:

a frame;

a CT imaging unit mounted to the frame, wherein the CT imaging unit is adapted to scan anatomical objects and generate images of the same;

a transport mechanism mounted to the frame, wherein the transport mechanism comprises a fine movement mechanism for moving the CT imaging unit precisely, relative to the patient, during scanning;

an on-board networking unit mounted to the frame, wherein the on-board networking unit is adapted to connect the CT imaging unit to a workstation, hospital PACs system or other IT network without requiring the use of conventional physical cabling during the same; and an on-board power unit mounted to the frame, wherein the on-board power unit is adapted to provide the electrical power needed to operate the CT imaging unit, transport mechanism and networking unit without requiring the use of conventional physical cabling during the same.

In another form of the present invention, there is provided a mobile imaging system comprising:

a frame;

a imaging unit mounted to the frame, wherein the imaging unit is adapted to scan anatomical objects and generate images of the same;

a transport mechanism mounted to the frame, wherein the transport mechanism comprises a fine movement mechanism for moving the imaging unit precisely, relative to the patient, during scanning;

an on-board networking unit mounted to the frame, wherein the on-board networking unit is adapted to connect the imaging unit to a workstation, hospital PACs system or other IT network without requiring the use of conventional physical cabling during the same; and an on-board power unit mounted to the frame, wherein the on-board power unit is adapted to provide the electrical power needed to operate the imaging unit, transport mechanism and networking unit without requiring the use of conventional physical cabling during the same.

In another form of the present invention, there is provided a mobile imaging system comprising:

a frame;

a imaging unit mounted to the frame, wherein the imaging unit is adapted to scan anatomical objects and generate images of the same;

a transport mechanism mounted to the frame, wherein the transport mechanism comprises a fine movement mechanism for moving the imaging unit precisely, relative to the patient, during scanning; and an on-board power unit mounted to the frame, wherein the on-board power unit is adapted to provide the electrical power needed to operate the imaging unit and transport mechanism without requiring the use of conventional physical cabling during the same.

In another form of the present invention, there is provided a mobile imaging system comprising:

a frame;

a imaging unit mounted to the frame, wherein the imaging unit is adapted to scan anatomical objects and generate images of the same;

a transport mechanism mounted to the frame, wherein the transport mechanism comprises a fine movement mechanism for moving the imaging unit precisely, relative to the patient, during scanning; and an on-board networking unit mounted to the frame, wherein the on-board networking unit is adapted to connect the imaging unit to a workstation, hospital PACs system or other IT network without requiring the use of conventional physical cabling during the same.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The Mobile CT Imaging System In General

Figure 1:
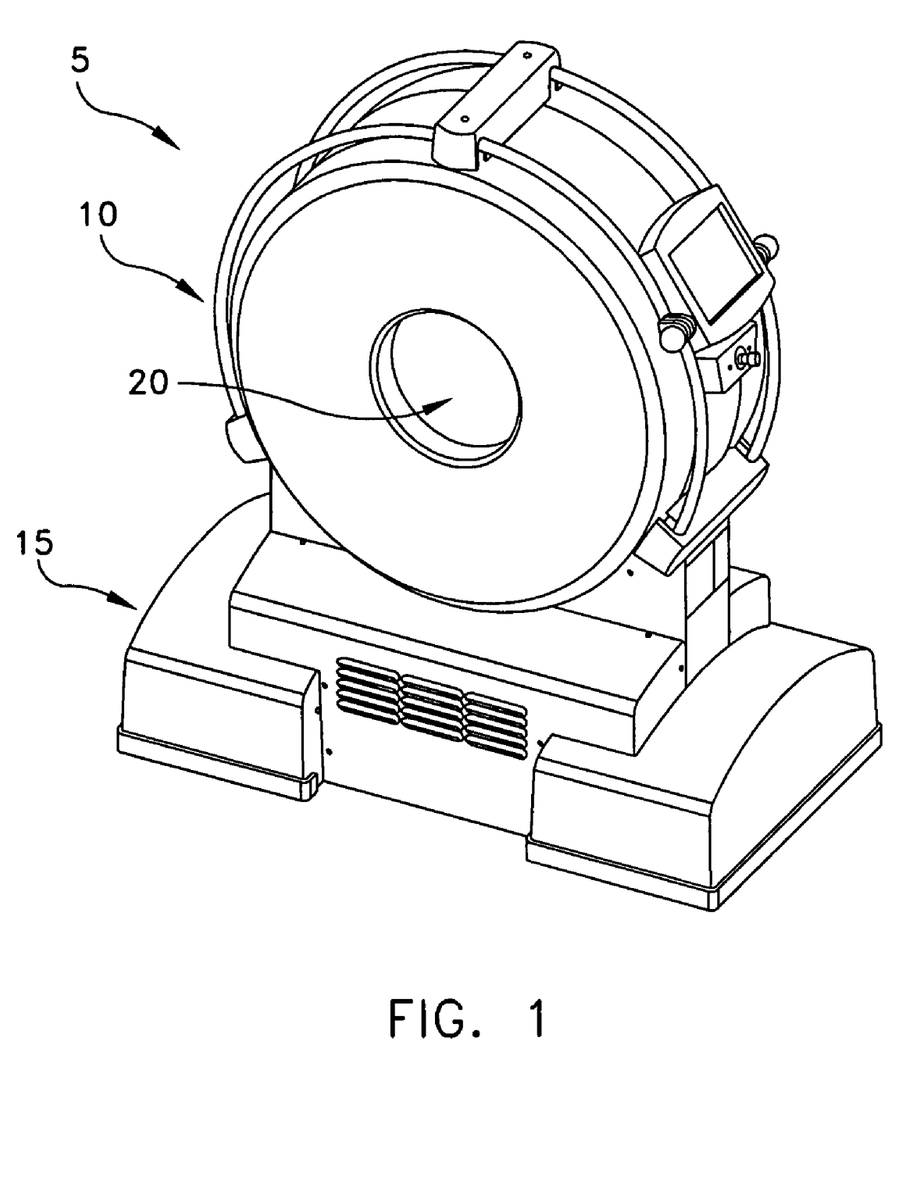
FIGS. 1 and 2 are schematic external views of a novel mobile CT imaging system formed in accordance with the present invention.
Figure 2:
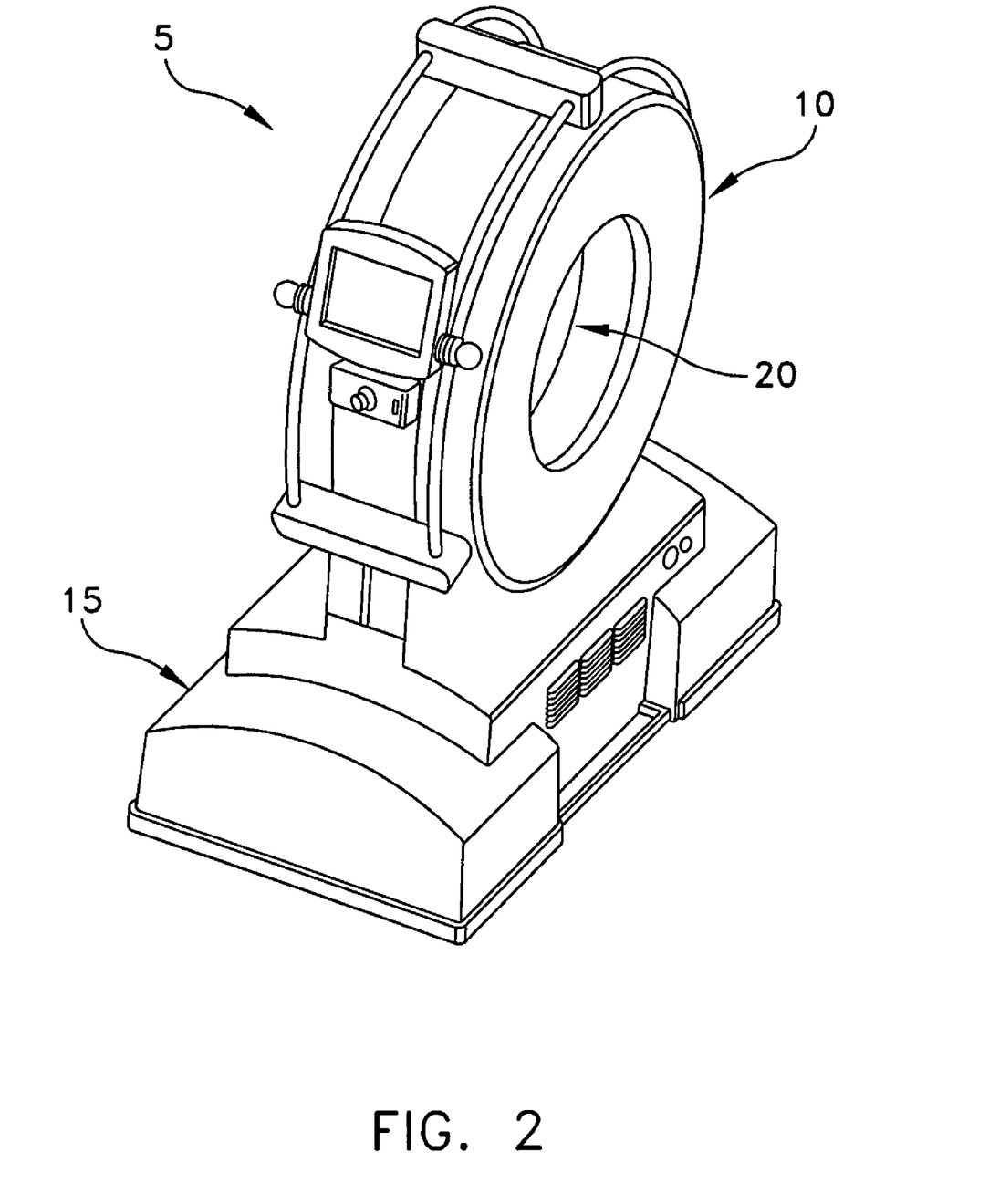

Looking first at FIGS. 1 and 2, there is shown a novel mobile CT imaging system 5 formed in accordance with the present invention. Mobile CT imaging system 5 generally comprises a torus 10 which is supported by a base 15. Torus 10 and base 15 together comprise a frame for mobile CT imaging system 5. A center opening 20 is formed in torus 10. Center opening 20 receives the patient anatomy which is to be scanned, i.e., the head of the patient when mobile CT imaging system 5 is to be used in stroke applications.

Figure 3:
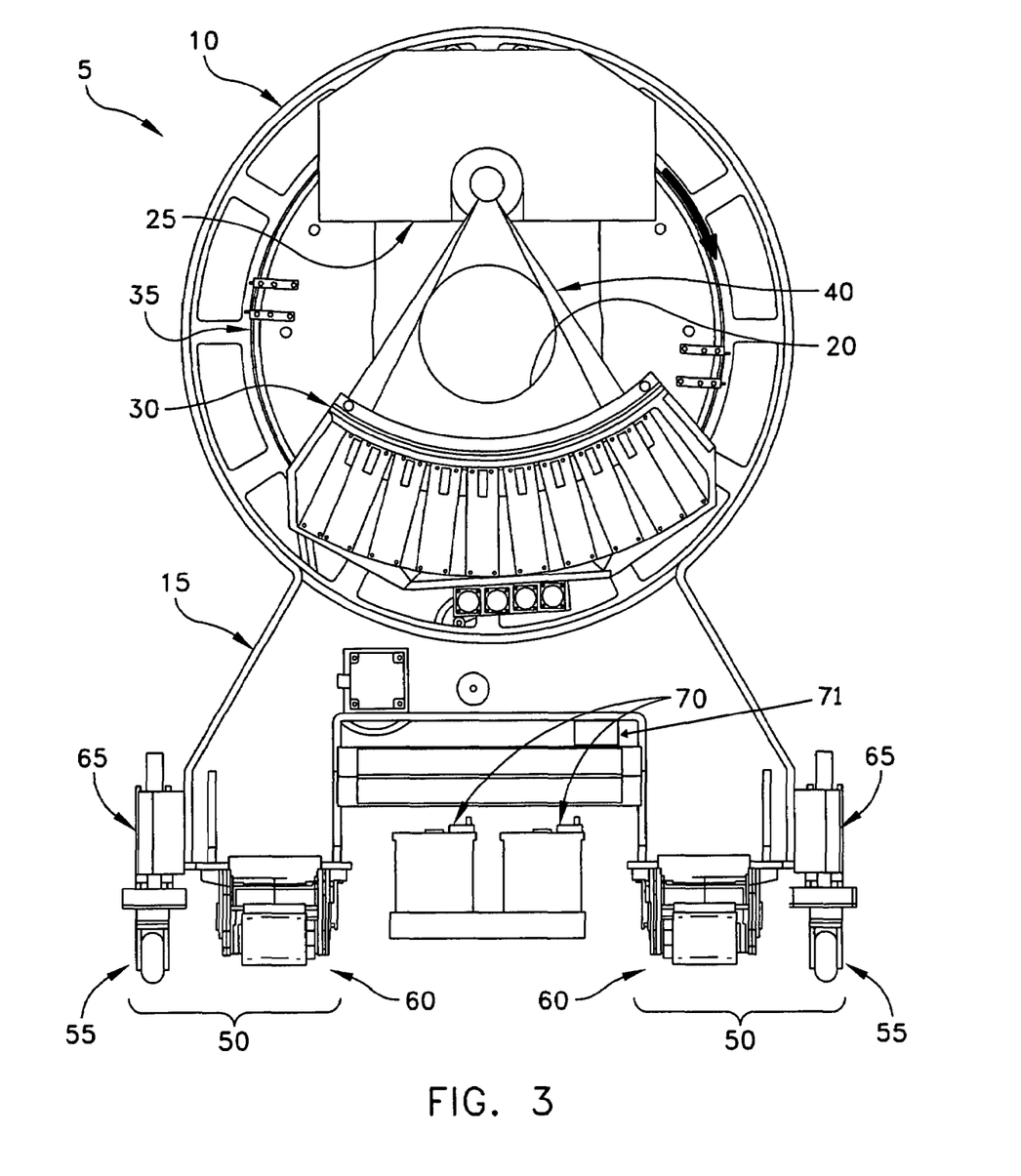
FIG. 3 is a schematic internal view of the novel mobile CT imaging system shown in FIGS. 1 and 2.

Looking next at FIG. 3, torus 10 generally comprises a X-ray tube assembly 25, an X-ray detector assembly 30, and a rotating drum assembly 35. X-ray tube assembly 25 and X-ray detector assembly 30 are mounted to the rotating drum assembly 35 in diametrically-opposing relation, such that the X-ray beam 40 (generated by X-ray tube assembly 25 and detected by X-ray detector assembly 30) is passed through the patient anatomy disposed in center opening 20. Furthermore, since X-ray tube assembly 25 and X-ray detector assembly 30 are mounted on the rotating drum assembly 35 so that they are rotated concentrically about center opening 20, the X-ray beam 40 will be passed through the patient's anatomy along a full range of radial positions, so as to enable the mobile CT imaging system 5 to create the desired computer model of the scanned anatomy.

The various electronic hardware and software for controlling the operation of X-ray tube assembly 25, X-ray detector assembly 30, and rotating drum assembly 35, as well as for processing the acquired scan data so as to generate the desired computer model, may be of the sort well known in the art and may be located in torus 10 and/or base 15.

Still looking now at FIG. 3, base 15 comprises a transport assembly 50 for moving mobile CT imaging system 5 about relative to the patient. More particularly, as disclosed in the aforementioned U.S. patent application Ser. No. 11/193,941, which patent application is hereby incorporated herein by reference, transport assembly 50 preferably comprises (i) a gross movement mechanism 55 for moving mobile CT imaging system 5 relatively quickly across room distances, so that the mobile CT imaging system can be quickly and easily brought to the patient, and (ii) a fine movement mechanism 60 for moving the mobile CT imaging system precisely, relative to the patient, during scanning, so that the patient can be scanned without being moved. As discussed in detail in the aforementioned U.S. patent application Ser. No. 11/193,941, gross movement mechanism 55 preferably comprises a plurality of free-rolling casters, and fine movement mechanism 60 preferably comprises a plurality of centipede belt drives (which can be configured for either stepped or continuous motion, whereby to provide either stepped or continuous scanning). Hydraulic apparatus 65 permits either gross movement mechanism 55 or fine movement mechanism 60 to be engaged with the floor, whereby to facilitate appropriate movement of mobile CT imaging system 5. However, as also discussed in detail in the aforementioned U.S. patent application Ser. No. 11/193,941, gross movement mechanism 55 may be omitted entirely, and only fine movement mechanism 60 may be provided, in which case fine movement mechanism 60 is used to both (i) move mobile CT imaging system 5 to the patient prior to scanning, and (ii) move the mobile CT imaging system relative to the patient during scanning.

Mobile CT imaging system 5 also comprises cordless and wireless capabilities, such that the mobile CT imaging system does not require physical cabling to (i) provide the electrical power needed to operate the mobile CT imaging system, and (ii) connecting the mobile CT imaging system to a workstation, hospital PACs system or other IT network.

More particularly, and as will hereinafter be discussed in further detail below, mobile CT imaging system 5 also comprises a novel on-board power unit 70 for providing the electrical power needed to operate the mobile CT imaging system without requiring the use of conventional physical cabling during the same, and a novel on-board networking unit 71 for connecting the mobile CT imaging system to a workstation, hospital PACs system or other IT network without requiring the use of conventional physical cabling during the same.

On-Board Power Unit 70

As noted above, and looking now at FIGS. 3 and 4, mobile CT imaging system 5 comprises an on-board power unit 70 for providing the electrical power needed to operate the mobile CT imaging system without requiring the use of conventional physical cabling during the same. The provision of such an on-board power unit has been heretofore unnecessary, inasmuch as conventional CT scanners are fixed-position devices which can have their power cabling carefully arranged at the time of CT scanner installation so as to make the power cabling relatively inobtrusive (e.g., the power cabling can be carefully positioned so that it is out of the way of patients and medical personnel). However, mobile CT imaging system 5 is intended to be quickly and easily deployed in critical-care situations where there is seldom time to carefully arrange the power cabling so as to keep it out of the way. Thus, the creation of a mobile CT imaging system has now created the need for a novel on-board power unit for providing the electrical power needed to operate the mobile CT imaging system without requiring the use of conventional physical cabling during the same. On-board power unit 70 is designed to address this need.

Figure 4:
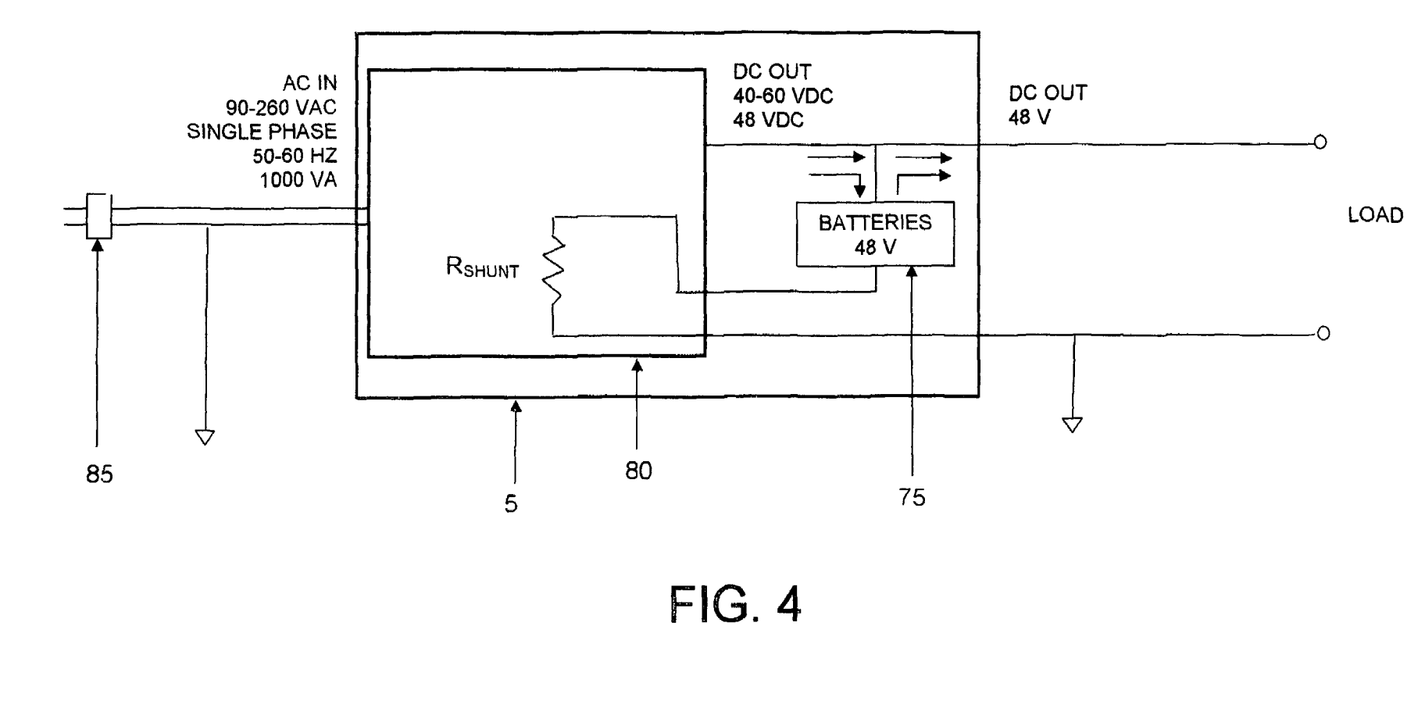
FIG. 4 is a schematic view showing a novel on-board power unit for providing the electrical power needed to operate the mobile CT imaging system without requiring the use of conventional physical cabling during the same.

Looking now at FIG. 4, on-board power unit 70 comprises one or more batteries 75 configured to output the electrical power needed to operate mobile CT imaging system 5. In one preferred form of the invention, mobile CT imaging system 5 requires 48 V DC, and batteries 75 comprises four 12 V batteries. Batteries 75 are preferably of the sort well known in the art.

On-board power unit 70 also comprises a transformer/charger 80. Transformer/charger 80 is constructed so that when the on-board power unit's plug 85 is plugged into a standard wall outlet, transformer/charger 80 will charge batteries 75. By way of example but not limitation, transformer/charger 80 may be configured to take 90-260 V, single phase, 50-60 Hertz AC power and convert it to 48 VDC power. Thus, between uses, mobile CT imaging system 5 may be positioned next to a standard wall outlet and plug 85 used, in conjunction with transformer/charger 80, to charge batteries 75. When mobile CT imaging system 5 is thereafter to be used, plug 85 is unplugged from the wall outlet, and then the mobile CT imaging system is moved (i.e., using transport assembly 50) to the patient for scanning.

In some circumstances it may be acceptable to use mobile CT imaging system 5 while plug 85 is plugged into a standard wall outlet. To this end, on-board power unit 70 is also configured so that when plug 85 is plugged into a wall outlet, mobile CT imaging system 5 will draw power directly from transformer/charger 80, with or without also drawing power out of batteries 75.

On-board power unit 70 is mounted to the frame of mobile CT imaging system 5 so that the on-board power unit will move with the remainder of the system. In one preferred form of the invention, on-board power unit 70 is mounted in base 15.

On-Board Networking Unit 71

As noted above, and looking now at FIGS. 3 and 5, mobile CT imaging system 5 comprises a novel on-board networking unit 71 for connecting the mobile CT imaging system to a workstation, hospital PACs system or other IT network without requiring the use of conventional physical cabling during the same.

The provision of such an on-board networking unit has been heretofore unnecessary, inasmuch as conventional CT scanners are fixed-position devices which can have their network cabling carefully arranged at the time of CT scanner installation so as to make the network cabling relatively inobtrusive (e.g., the network cabling can be carefully positioned so that it is out of the way of patients and medical personnel). However, mobile CT imaging system 5 is intended to be quickly and easily deployed in critical-care situations where there is seldom time to carefully arrange the network cabling so as to keep it out of the way. Thus, the creation of a mobile CT imaging system has now created the need for a novel on-board networking unit for connecting the mobile CT imaging system to a workstation, hospital PACs system or other IT network without requiring the use of conventional physical cabling during the same.

Figure 5:
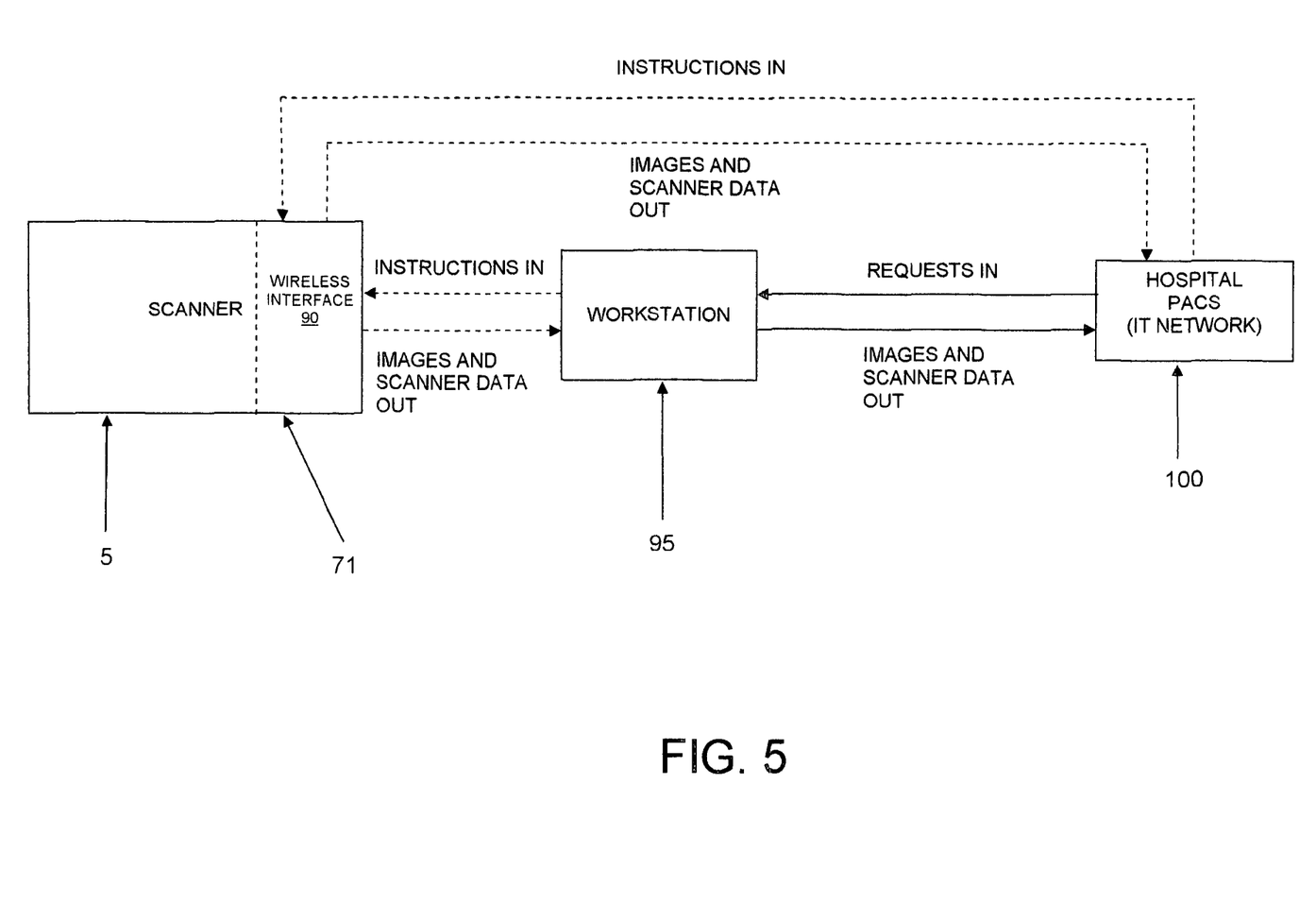
FIG. 5 is a schematic view showing a novel on-board networking unit for connecting the mobile CT imaging system to a workstation, hospital PACs system or other IT network without requiring the use of conventional physical cabling during the same.

Looking now at FIG. 5, on-board networking unit 71 comprises a wireless interface 90 configured to wirelessly connect mobile CT imaging system 5 to a workstation 95, whereby to permit medical personnel to issue scanning instructions to mobile CT imaging system 5 using the workstation, and whereby to enable the mobile CT imaging system to send images and scanner data to the workstation for viewing by medical personnel. Workstation 95 can, in turn, be connected to a hospital PACs system or other IT network 100, so as to permit mobile CT imaging system 5 to be controlled from remote locations and so as to permit images and scanner data to be viewed by medical personnel at remote locations. Alternatively, wireless interface 90 can be directly connected to the hospital PACs system or other IT network 100.

Wireless interface 90 is preferably of the sort well known in the art, e.g., a WIFI interface conforming to appropriate IEEE standards such as 802.11b, 802.11g, etc.

On-board networking unit 71 is mounted to the frame of mobile CT imaging system 5 so that the on-board networking unit will move with the remainder of the system. In one preferred form of the invention, on-board networking unit 71 is mounted in base 15.

Use

Mobile CT imaging system 5 is preferably used as follows.

When not in use, mobile CT imaging system 5 is preferably stored in the emergency room (or other intended place of use), in an out-of-the-way location, raised on its gross movement mechanism 55 (i.e., its casters), and with its plug 85 plugged into a standard wall outlet so that batteries 75 are fully charged.

When a patient arrives at the emergency room presenting stroke-like symptoms, the patient is quickly scanned in the emergency room, on their gurney, using mobile CT imaging system 5. More particularly, mobile CT imaging system 5 is unplugged from the wall, and the CT imaging system is then moved on its casters to the patient, so that the patient (while still lying on their gurney) is positioned within the center opening 20 of CT imaging system 5. Thereafter, using on-board power unit 70, hydraulic apparatus 65 is activated so that CT imaging system 5 is supported on its fine movement mechanism 60 (i.e., the centipede belt drives). Using on-board power unit 70 and on-board networking unit 71, scanning is then commenced, with fine movement mechanism 60 precision-advancing CT machine 5 relative to the patient during scanning. Image data is off-loaded (to work station 95, and/or the hospital PACs system or other IT network 100 using on-board networking unit 71.

Thus, with the present invention, there is provided a novel mobile CT machine with cordless and wireless capabilities, such that the novel CT machine does not require physical cabling to (i) provide the electrical power needed to operate the mobile CT scanner, and (ii) connecting the CT scanner to a workstation, hospital PACs system or other IT network.

Application To Other Types Of Scanning Systems

It should be appreciated that the present invention is not limited to use in medical applications or, indeed, to use with CT machines. Thus, for example, the present invention may be used in connection with CT machines used for non-medical applications, e.g., with CT machines which are used to scan inanimate objects. Furthermore, the present invention may be used with non-CT-type scanning systems. In essence, the present invention has application to any mobile scanning device which requires cordless and wireless operation.

MODIFICATIONS

It will be appreciated that still further embodiments of the present invention will be apparent to those skilled in the art in view of the present disclosure. It is to be understood that the present invention is by no means limited to the particular constructions herein disclosed and/or shown in the drawings, but also comprises any modifications or equivalents within the scope of the invention.

What is claimed is:

1. A mobile CT imaging system comprising:
a frame;
a CT imaging unit mounted to the frame, wherein the CT imaging unit is adapted to scan anatomical objects and generate images of the same;
a transport mechanism mounted to the frame, wherein the transport mechanism comprises a fine movement mechanism for moving the CT imaging unit precisely, relative to the patient, during scanning;
an on-board networking unit mounted to the frame, wherein the on-board networking unit is adapted to connect the CT imaging unit to a workstation, hospital PACs system or other IT network without requiring the use of conventional physical cabling during the same; and
an on-board power unit mounted to the frame, wherein the on-board power unit is adapted to provide the electrical power needed to operate the CT imaging unit, transport mechanism and networking unit without requiring the use of conventional physical cabling during the same.

2. A mobile CT imaging system according to claim 1 wherein the fine movement mechanism is configured to move the mobile CT imaging system relative to the patient using indexed movement in discrete steps, whereby to enable slice scanning.

3. A mobile CT imaging system according to claim 1 wherein the fine movement mechanism is configured to move the mobile CT imaging system relative to the patient using substantially continuous movement, whereby to enable helical scanning.

4. A mobile CT imaging system according to claim 1 wherein the fine movement mechanism comprises at least one centipede belt drive unit.

5. A mobile CT imaging system according to claim 4 wherein the fine movement mechanism comprises two centipede belt drive units.

6. A mobile CT imaging system according to claim 5 wherein one centipede belt drive unit is disposed on either side of the patient.

7. A mobile CT imaging system according to claim 1 wherein the transport mechanism further comprises a gross movement mechanism for transporting the mobile CT imaging system relatively quickly across room distances.

8. A mobile CT imaging system according to claim 7 wherein the gross movement mechanism comprises at least one caster unit.

9. A mobile CT imaging system according to claim 8 wherein the gross movement mechanism comprises two caster units, each having two caster wheels.

10. A mobile CT imaging system according to claim 9 wherein one caster unit is disposed on either side of the patient.

11. A mobile CT imaging system according to claim 7 wherein the transport mechanism is configured so that the mobile CT imaging system is: (i) transported by the gross movement mechanism while the mobile CT imaging system is being moved across room distances to the patient; and (ii) moved precisely relative to the patient by the fine movement mechanism while the patient is being scanned by the mobile CT imaging system.

12. A mobile CT imaging system according to claim 7 wherein the gross movement mechanism comprises an actuator for: (i) extending portions of the gross movement mechanism below portions of the fine movement mechanism whereby the mobile CT imaging system will be supported by portions of the gross movement mechanism; and (ii) retracting portions of the gross movement mechanism above portions of the fine movement mechanism whereby the mobile CT imaging system will be supported by portions of the fine movement mechanism.

13. A mobile imaging system comprising:
a frame;
a imaging unit mounted to the frame, wherein the imaging unit is adapted to scan anatomical objects and generate images of the same;
a transport mechanism mounted to the frame, wherein the transport mechanism comprises a fine movement mechanism for moving the imaging unit precisely, relative to the patient, during scanning;
an on-board networking unit mounted to the frame, wherein the on-board networking unit is adapted to connect the imaging unit to a workstation, hospital PACs system or other IT network without requiring the use of conventional physical cabling during the same; and
an on-board power unit mounted to the frame, wherein the on-board power unit is adapted to provide the electrical power needed to operate the imaging unit, transport mechanism and networking unit without requiring the use of conventional physical cabling during the same.

14. A mobile imaging system comprising:
a frame;
a imaging unit mounted to the frame, wherein the imaging unit is adapted to scan anatomical objects and generate images of the same;
a transport mechanism mounted to the frame, wherein the transport mechanism comprises a fine movement mechanism for moving the imaging unit precisely, relative to the patient, during scanning; and
an on-board power unit mounted to the frame, wherein the on-board power unit is adapted to provide the electrical power needed to operate the imaging unit and transport mechanism without requiring the use of conventional physical cabling during the same.

15. A mobile imaging system comprising:
a frame;
a imaging unit mounted to the frame, wherein the imaging unit is adapted to scan anatomical objects and generate images of the same;
a transport mechanism mounted to the frame, wherein the transport mechanism comprises a fine movement mechanism for moving the imaging unit precisely, relative to the patient, during scanning; and
an on-board networking unit mounted to the frame, wherein the on-board networking unit is adapted to connect the imaging unit to a workstation, hospital PACs system or other IT network without requiring the use of conventional physical cabling during the same.

* * * * *